United States Patent [19]

Lewis et al.

[11] Patent Number: 6,039,726

[45] Date of Patent: *Mar. 21, 2000

[54] METHOD AND APPARATUS FOR CONCENTRATING LASER BEAMS

[75] Inventors: Aaron Lewis; Daniel Palanker; Igor Turovets, all of Jerusalem, Israel

[73] Assignee: Nanoptics, Inc., Jerusalem, Israel

[*] Notice: This patent issued on a continued prosecution application filed under 37 CFR 1.53(d), and is subject to the twenty year patent term provisions of 35 U.S.C. 154(a)(2).

[21] Appl. No.: 08/676,223

[22] PCT Filed: Jan. 23, 1995

[86] PCT No.: PCT/US95/00540

§ 371 Date: Oct. 15, 1996

§ 102(e) Date: Oct. 15, 1996

[87] PCT Pub. No.: WO95/19811

PCT Pub. Date: Jul. 27, 1995

[51] Int. Cl.[7] ....................................................... A61N 5/06

[52] U.S. Cl. .................................. 606/3; 606/10; 606/13; 606/16

[58] Field of Search ............................ 606/2–19; 385/33, 385/15

[56] References Cited

U.S. PATENT DOCUMENTS

| | | |
|---|---|---|
| 3,348,547 | 10/1967 | Kavanagh . |
| 3,670,260 | 6/1972 | Koester ..................................... 606/10 |
| 4,641,912 | 2/1987 | Goldenberg ............................... 606/7 |
| 4,686,979 | 8/1987 | Gruen et al. .............................. 606/3 |
| 5,044,717 | 9/1991 | Levatter .................................. 385/33 |
| 5,201,730 | 4/1993 | Easley et al. ............................. 606/4 |
| 5,288,288 | 2/1994 | Lewis et al. ............................. 606/14 |

*Primary Examiner*—David M. Shay
*Attorney, Agent, or Firm*—Jones, Tullar & Cooper PC

[57] ABSTRACT

The invention includes the use of a beam homogenizer (scattering surface) at the input aperture of a tapered optical fiber to avoid hot spots (2) in the tapered section which would otherwise destroy the fiber (10).

11 Claims, 6 Drawing Sheets

METHOD AND APPARATUS FOR CONCENTRATING LASER BEAMS

1. FIELD OF THE INVENTION

The invention is a method and a device that allows for high speed and high precision cutting of biological tissues in a liquid environment with minimal physiological damage to the surrounding tissue.

2. BACKGROUND OF THE INVENTION

Lasers have been shown to be effective and convenient surgical tools. Among the variety of possible surgical lasers the ArF excimer laser has been found to be the best choice for producing precise cuts during tissue removal in a gaseous environment without collateral damage to the surrounding tissue layers (C. A. Puliafito, R. F. Steinert, T. F. Deutch, F. Hillencamp, E. F. Dehm, C. M. Adler, Ophthalmol. 92, 741(1985); S. L. Jacques, D. J. McAulitte, I. H. Blank and J. A. Parrish, J. Inv. Derm. 88, 88(1987); J. Marshall, S. Trokel, S. Rothery and R. Krueger, British J. Ophthalmol. 70, 487(1986). This considerable advantage of the ArF excimer laser is based on a photochemical, rather than thermal, mechanism of the tissue removal (R. Srinivasan, P. E. Dyer, B., Braven, Lasers Surg. Med. 6, 514(1987)). The energy of the 193 nm photon is sufficient for breaking almost all chemical bonds in biological compounds. This fast photochemical reaction followed by fast tissue removal prevents heat deposition and other side effects caused by other lasers. Up to now all surgical applications of the ArF excimer laser were based on the treatment of tissue surface in an air environment. Excellent results were obtained, for example, in refractive surgery (F. A. L'Esperance, J. W. Warner, William B. Telfair, P. R. Roger, C. A. Martin, Arch. ophtalmol., 107, 131(1989)) and skin treatment (S. L. Jacques, D. J. McAulitte, I. H. Blank and J. A. Parrish, J. Inv. Derm. 88, 88(1987)).

During the last few years new methods based on fiber optic delivery systems have been developed for laser angioplasty (T. G. van Leeuwen, L. van Erven, J. H. Meertence, M. Motamedi, M. J. Post, C. Burst, J.Am. Coll. Cardiol., 19, 1610(1992); T. Tomary, H. J. Geschwind, G. Boussignac, F. Lange, S. J. Tank, Am. Hear J., 123, 8861992)), bone and cartilage cutting and drilling (M. Dressel, R. Jahn, W. New and K. H. Jungbluth Lasers Surg. Med., 11, 569(1991)), and other surgical applications. These methods are simple, convenient and allow the delivery of a laser beam to the required position in a liquid environment. The laser wavelength ranges being transmitted through these fibers were mainly associated with the spectral range of the fiber's transmittance, which is the mid IR, visible and near UV and thus, these wavelengths were used for tissue cutting even though such wavelengths are not the optimum for tissue removal. In all such tissue removal applications with these laser wavelengths different measures of thermal injury or shock waves caused side effects in the surroundings of the lesion. The best results were obtained with the 308 nm excimer laser (T. G. van Leeuwen, L. van Erven, J. H. Meertence, M. Motamedi, J. J. Post, C. Burst, J.Am. Coll. Cardiol., 19, 1610(1992); T. Tomary, H. J. Geschwind, G. Boussignac, F. Lange, S. J. Tank, Am. Heart J., 123 8861992)). But even in this case the mechanism of laser/tissue interaction was shown to be thermal. All attempts to effectively deliver the ArF excimer laser beam through quartz fibers failed because of both the non-linear absorption at high intensities and induced color centers formation at this wavelength. As a result, at high radiation intensities and for multiple pulses quartz fibers were shown to become almost nontransparent (M. Dressel, R. Jahn, W. Neu and K.-H. Jungbluth Lasers Surg. Med., 11, 569(1991)).

Until recently only one method of the ArF laser delivery into a liquid environment was developed (A. Lewis and D. Palanker U.S. Pat. No. 5,288,288). The laser beam was guided through a hollow glass tapered micropipette, in which a gas was introduced at a pressure equal to the capillary force of the liquid at the pipette exit. The micropipette served at the same time as a beam guide, a concentrator and an aperture. This method allowed the drilling of precise and reproducible holes in the zona pellucida of oocytes for enhancement of sperm penetration (D. Palanker, S. Ohad, A. Lewis, A., Simon. J. Shenkar, S. Penchas and N. Layfer, Lasers Surg. Med., 11, 580(1991)). For this application the diameter of the tapered tip was about 8 microns and a low energy fluence was applied. For larger tips and a high energy fluence the method of static gas pressure is not effective for maintenance of an air/liquid boundary at the exit of the tip.

The instrument we have devised overcomes all of the problems of ArF laser delivery to a tissue in a highly absorbing liquid environment and allows the cutting of materials with high speed and high precision without observable heat injury.

3. STATE OF PRIOR ART

The ArF excimer laser was applied in medicine until recently for refractive surgery (J. Marshall, S. Trokel, S. Rothery and R. Krueger, British J. Ophthalmol., 70, 487 (1986); F. A. L'Esperance J. W. Warner, William B. Telfair, P. R. Roger, C. A. Martin, Arch. Ophthalmol., 107, 131–139 (1989), skin treatment (S. L. Jacques, D. J. McAulitte, I. H. Blank and J. A. Parrish, J. Inv. Derm. 88, 88(1987)), and in-vitro fertilization (D. Palanker, S. Ohad, A. Lewis, A. Simon, J. Shenkar, S. Penchas and N. Layfer, Lasers Surg. Med., 11, 580(1991)). The first two techniques are applicable only to dry surface treatments and are not suitable for surgery of internal organs and tissues covered by biological liquids. The last approach is not suitable for tissue microsurgery because it is based on the use of glass air-filled micropipettes. These pipettes are not applicable if the tip diameters exceed 20 microns, since it is difficult to maintain positive air pressure in the micropipette to prevent liquid from entering. The pipettes also cannot withstand high energy fluences and are rather brittle. Thus, with the ArF excimer, microsurgical operations of internal organs and tissues covered by biological liquids were not performed.

4. SUMMARY OF THE INVENTION

A device and a method that allows for flexible delivery, concentration and aperturing of the ArF excimer laser beam and enables soft tissues microsurgery in liquid or gaseous environments. The device consists of three main elements:

a concentrator of energy;

a beam homogenizer, and a flexible delivery system.

In addition, this device is able to deliver a variety of other laser beams permitting parallel operations to be performed.

5. BRIEF DESCRIPTION OF THE DRAWINGS

The various objects, features and advantages of the present invention will be apparent to those of skill in the art from the following detailed description of a preferred embodiment, taken with the accompanying drawings, in which.

6. DESCRIPTION OF THE INVENTION

All the fibers available until now for the deep ultraviolet close to the vacuum ultraviolet are made from UV grade fused silica. The very high nonlinear absorption coefficient of this material at 193 nm (R. K. Brimacombe, R. S. Tailor and K. E. Leopold, J. Appl. Phys., 66 4035(1989)) limits the energy output. Even for intravitreal surgery when the minimal length of a fiber can be about 4.5 cm, it is impossible to obtain enough energy fluence at the tip of such a fiber. Fiberguide G fibers, for example, allow the delivery through this length of only a 160 mJ/cm$^2$/pulse when the energy fluence at the entrance approaches the damage threshold of fused silica (<$F_{thresh}$ (193 nm)>=1500 mJ/cm$^2$/pulse). Such an energy fluence is not enough for effective tissue cutting even for such soft tissues as the retina and epiretinal membranes (A. Lewis, D. Palanker, I. Hemo, J. Pe'er and H. Zauberman, Invest. Ophthalmol. Vis. Sci., 33, 2377(1992)). In order to overcome this problem, we developed a method and a device to convert the best fused silica fibers into a conical concentrator with a specially tapered tip at an entrance surface that enables an increase in the output energy fluence up to the level required for effective tissue cutting.

6.1. Beam Concentrator

Figure 1:
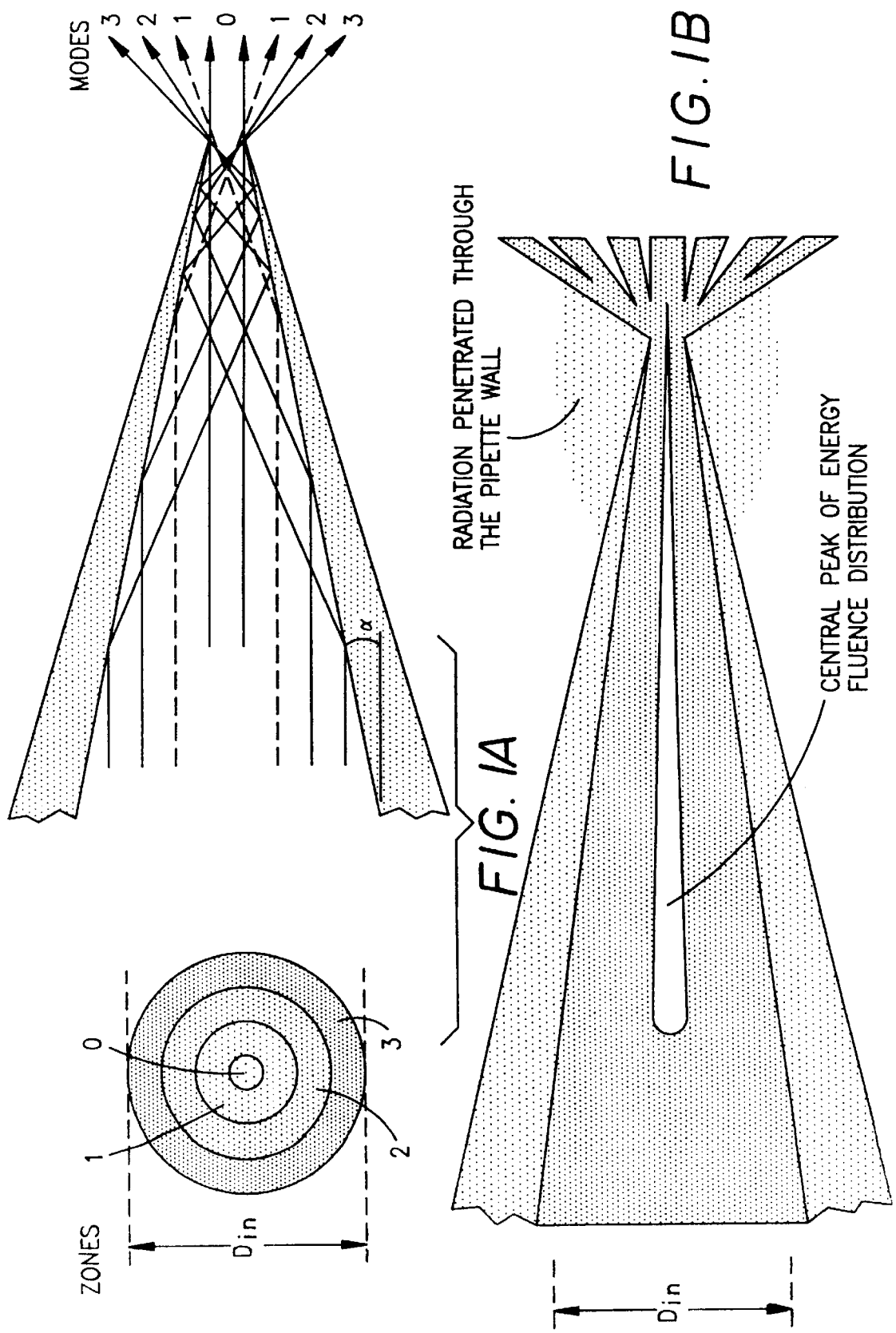
FIG. 1A illustrates a scheme of light propagation in a conical structure.
FIG. 1B is a schematic representation of the energy distribution in a conical structure.
Figure 2:
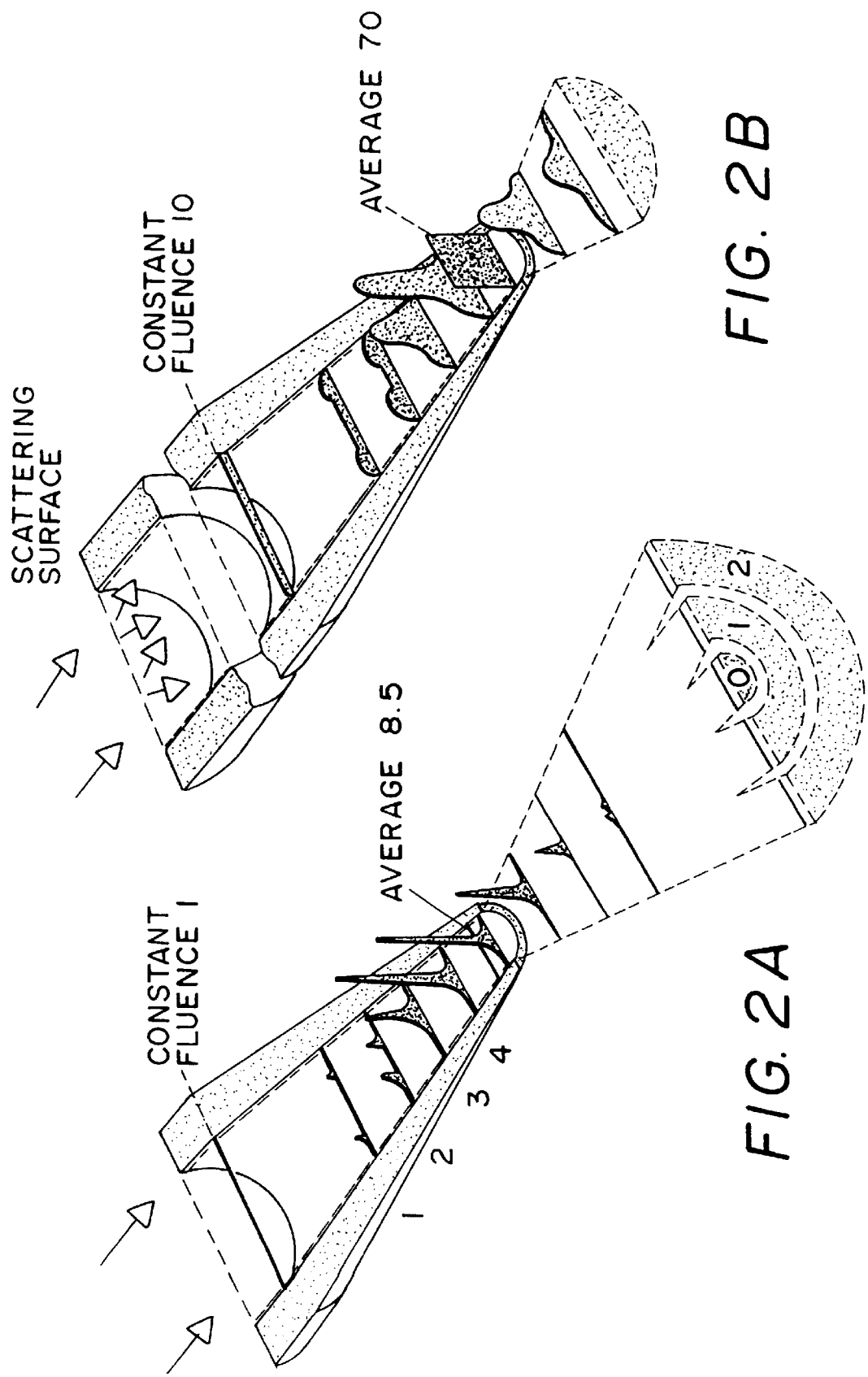
FIG. 2A is a schematic diagram of the beam energy fluence distribution inside and outside a conical tip having a polished entrance surface.
FIG. 2B is a schematic diagram if the beam energy fluence distribution inside and outside a conical tip having a scattering entrance surface (arrows indicate propagation direction)

Calculations were completed of the energy fluence distribution inside conical structures for a constant reflection coefficient (i.e.,. metal walls) in H. Schmidt-Kloiber and H. Schoeffman, Appl. Optics, 25, 252(1986), for a durable reflection coefficients—sapphire tip in a water environment in R. M. Verdaasdonk and C. Borst Appl. Optics., 30, 2172(1991) and for an air-filled glass pipette in D. Palanker and A. Lewis, unpublished. A scheme of light propagation through a cone 10 is shown in FIG. 1A, wherein the light will exit from the cone after different numbers of reflections (or modes 0,1 . . . ) depending on the distance of the incoming light from the optical axis (zones 0,1 . . . ). For simplicity in the drawing, only modes up to No. 3 are shown. FIG. 1B is a schematic representation of the energy distribution within cone 10. The energy fluence distribution of the beam inside and outside of the conical tip is shown qualitatively in FIG. 2A, which is a schematic diagram of a conical tip with a polished entrance surface. FIG. 2B is a schematic diagram of the beam energy fluence distribution with a scattering entrance surface. Energy fluence at the pipette entrance plane is assumed to be constant. The maximal peak intensity inside the core corresponds to the damage threshold of the fiber. The mean energy concentration coefficient for each mode of propagated light is proportional to the relationship of the enter/exit surface areas and to the appropriate reflection coefficients. An important feature of laser beam concentration in a conical structure is that the energy fluence distribution is highly non uniform, as illustrated in FIG. 2A. The energy fluence in the focusing area is inversely proportional to the distance from the optical axes and to the beam divergence. A central peak appears inside the cone when the first reflected rays reach an optical axis, and ends when the last reflected rays (mode 1) leave this axis, with its height inversely proportional to the beam divergence. In practice, at least three additional factors can influence the energy distribution and may even sharpen the energy peaks. They are: (1) non-coaxiality of the beam with the fiber axes, (2) gradual increase of the cone angle at the beginning of the cone, and (3) interference of the reflected rays inside the material.

Figure 3:
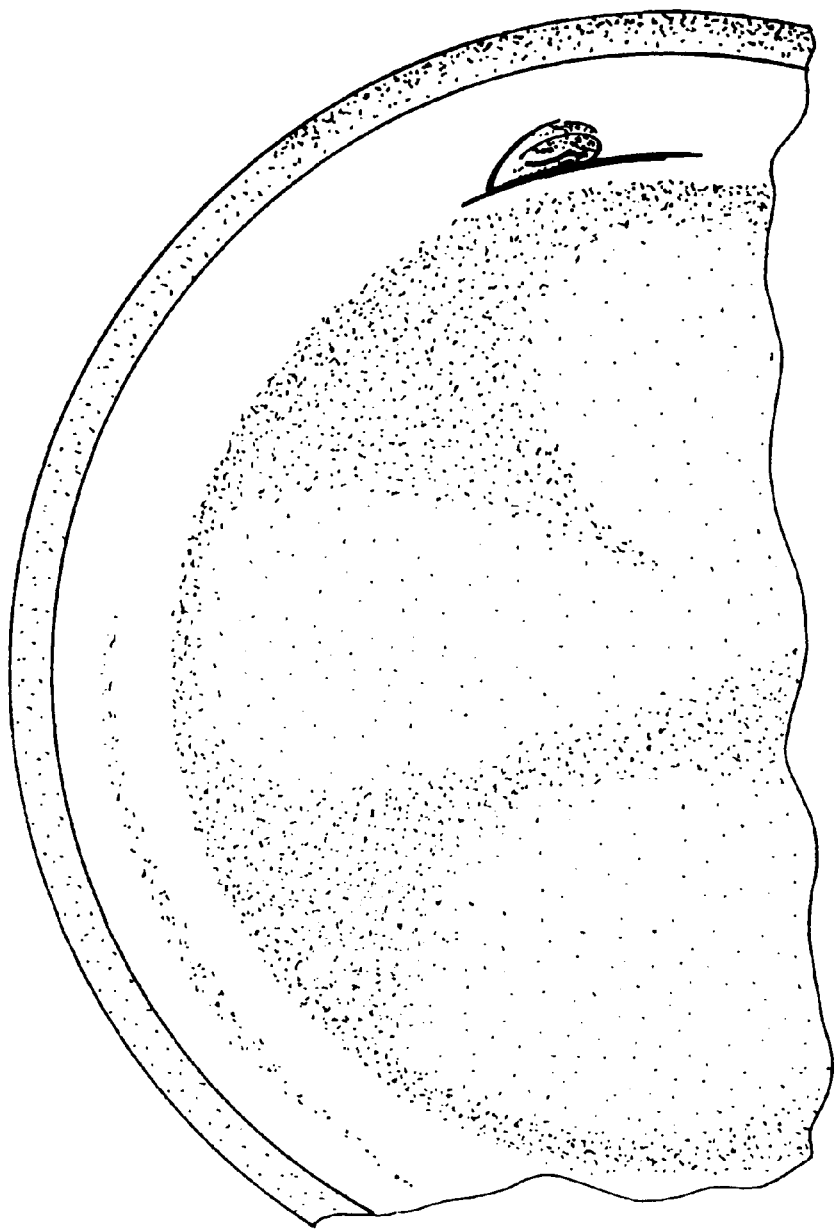
FIG. 3 is a micrograph of light exiting from a tapered fiber tip at the plane corresponding to the position of the circular peak (one or two) of FIG. 2A (arrow indicates excimer laser caused damage)

The cone remains transmitting unless the peak of energy fluence exceeds the damage threshold of the cone material. Since these peaks for a low divergence beam are rather sharp, the maximal average energy fluence transmitted through the fiber cannot be substantially increased by its tapering, or else the cone will be destroyed at its very beginning. For example, in the case of tips made from fused silica Fiberguide G fibers the destruction of the cone material in the bulk was found for the tip diameters of about 0.7 of the entrance diameter when the average output fluence was as low as 30 mJ/cm$^2$/pulse. In this case the destruction is caused by a circular energy peak, illustrated in FIGS. 2A and 2B and FIG. 3 at peak 2, even before the central peak formation. FIG. 3 is a micrograph, at a magnification of 200, of light exiting from the tapered fiber tip 10 at the plane which corresponds to the position of the circular peak 2 shown in FIG. 2A. The arrow indicates the excimer laser-caused damage, which is located at the same place as the peak of the energy fluence distribution. The exit diameter of the tapered fiber tip is 0.7 of the fiber diameter. For smaller exit diameters the tip will be destroyed at even lower mean energy fluence. Such a level of the energy fluence is not sufficient for an effective ablation of soft tissue, where an energy fluence of about 250 to 350 mJ/cm$^2$/pulse is required. In order to maximize the average energy delivered through the cone the distribution peaks inside should be broadened.

6.2 Beam Homogenizer

Figure 4A:
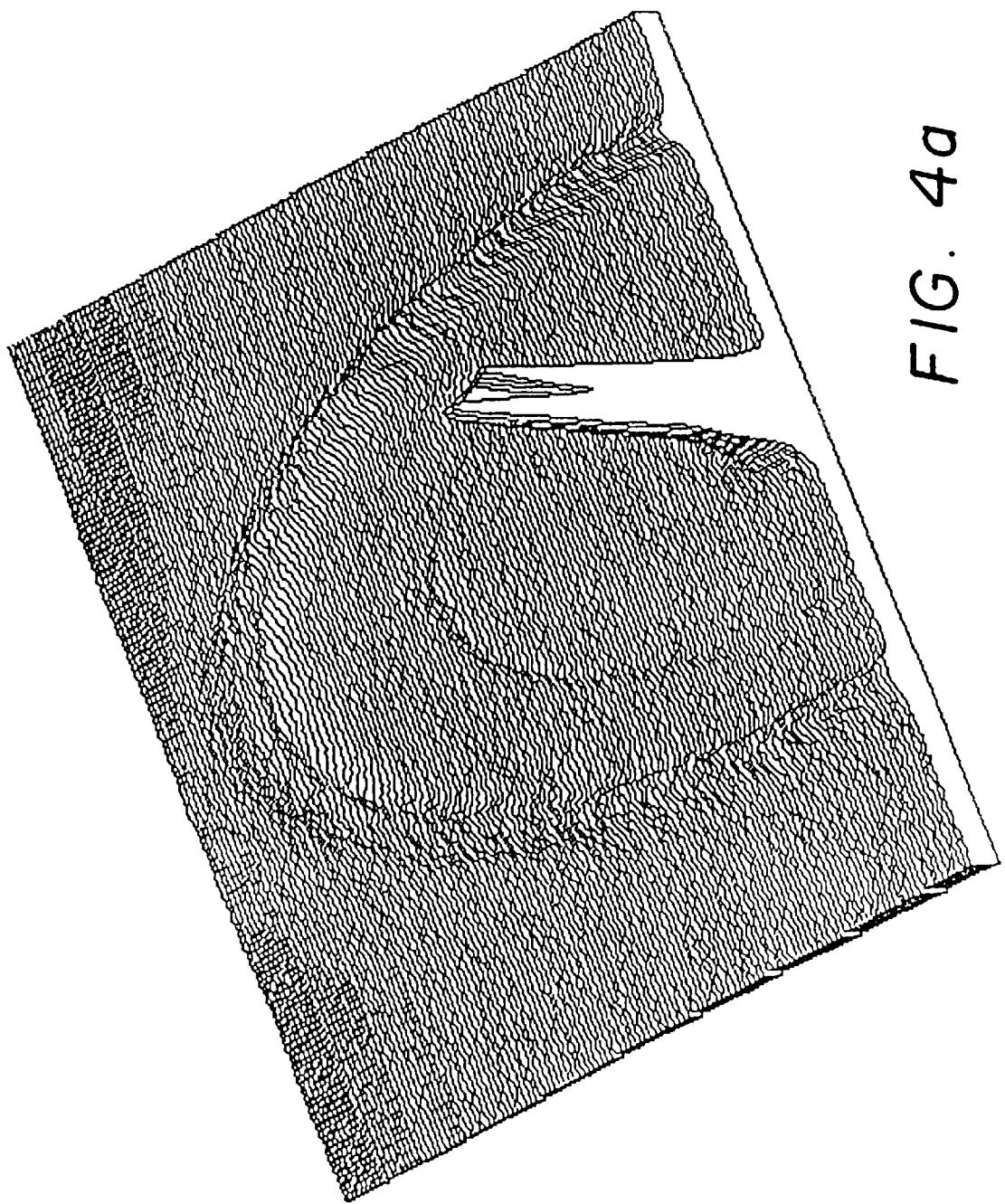
FIG. 4A is a 3-dimensional plot of the energy fluence distribution of an excimer laser beam exiting from a tapered tip with a polished entrance surface.
Figure 4B:
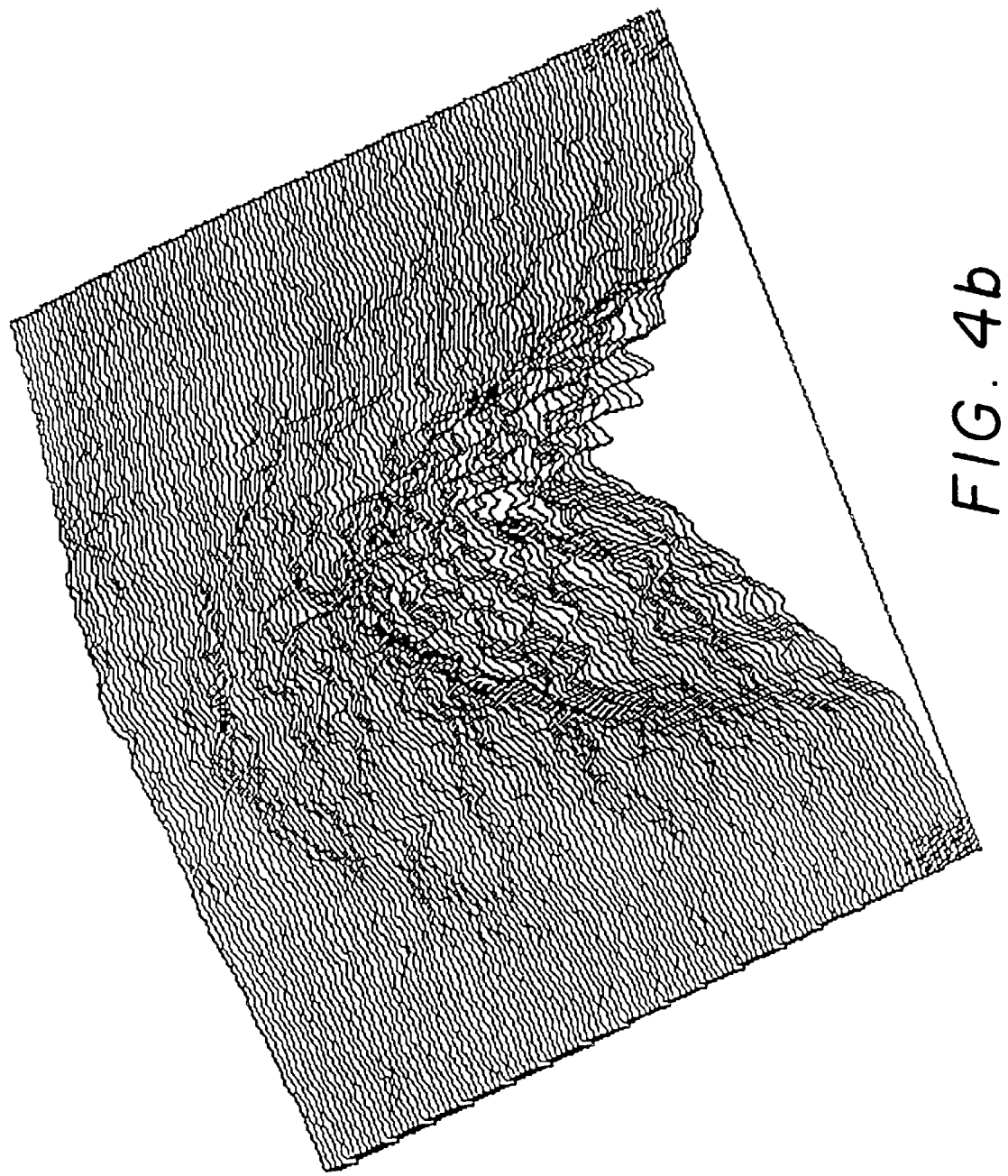
FIG. 4B is a 3-dimensional plot of the energy fluence distribution of an excimer laser beam exiting from a tapered tip with a ground entrance surface.

In order to broaden these peaks the entering beam divergence should be increased. This may be accomplished by scattering the beam through rough optical surface before entering the tip (see FIG. 2B). This may be carried out by an entering surface of the tip or by a surface of an additional plate placed before the tip. The angle distribution of the scattered beam depends on the roughness of that surface. Insertion of a scattering surface allows the use of fused silica fibers at rather high energy fluence without their destruction by hot spots of the energy inside the fiber as the result of either non ideal fiber orientation, inhomogeneity of the laser beam, or beam interference inside the fiber. A three-dimensional plot of the energy fluence distributions of the excimer laser beam exiting from the tapered tip are shown in FIGS. 4A and 4B for both a polished (4A) and a ground (4B) entrance surface. Grinding of the entrance surface was accomplished with the use of a grinding paper having a particle size of less than 20 microns. As can be seen in these Figures, such scattering lowers the intensity and broadens the peaks of the energy distribution, and this enables an increase of the entering energy. As a result, the total energy transmitted through the conical tip can be increased without damaging it.

On the other hand, the increasing beam divergence reduces the energy exiting from the conical tip since the reflection coefficient of the walls decreases as the angle of incidence increases beyond the angle of total internal reflection. This means that there is some optimal level of roughness of the scattering surface that enables delivery of a maximal energy throughput from the tip. This level is determined by the material's damage threshold, the cone's angle x, and a relation of the exit/entrance cone diameters. We found that for tips made from Fiberguide G fibers with the angle x~0.2 and an exit diameter of about 0.3 of the entrance diameter, the surface should be roughened by grinding paper with a maximal particle dimension of 20 microns. In this case insertion of the scattering surface decreases the energy output by only 33% but enables an increase of the entering and average transmitted energy by at least 10 times, as a result of broadening the peaks of the energy distribution. Thus, the addition of this optimal scattering surface enables the tips to deliver about 500 mJ/cm$^2$/pulse and this is enough for effective soft tissue cutting.

It should be mentioned that an additional concentric tube around a tapered tip through which a liquid is suctioned out could be used to mechanically protect the device, to lift the irradiated tissue by suction and to evacuate the gas bubbles and tissue debris that result from laser/tissue interactions.

6.3 Parameters for an All Fiber Flexible Delivery System.

In order to flexibly deliver the laser beam into a surgical field the special articulated arm described in U.S. Pat. No. 5,288,288 may be used. The large excimer laser beam is focused inside the articulated arm in order to obtain the required energy fluence on the exit of the arm and in order to use the beam in a more efficient way. A few requirements for the focusing system should be fulfilled. The beam dimensions at the exit of the arm should exceed the fiber diameter in order to compensate for beam shifts induced by the arm movements. The entering beam has to be rather parallel in order to be effectively concentrated in the fiber tip. These requirements could be fulfilled by either a long focal length lens inside the articulated arm, or a telescope that can be fixed at the arm's exit.

In the present system a long-focal length (500 mm) lens was placed inside the arm in order to concentrate the radiation on the entering surface of the tapered fiber to the required level (about 150 to 250 mJ/cm$^2$/pulse). The dimensions of the beam at the fiber entrance plane were 3×1.5 mm. Thus, in the case of a 1 mm core diameter, about 20% of the laser energy entered the fiber and was utilized for microsurgery.

Such an articulated arm could be used together with the herein-described new tip for flexible delivery of the ArF excimer laser for microsurgery in liquid environments. Nonetheless, it is apparent that efficiency of the energy transfer from the articulated arm to the fiber cannot be high, because of the above mentioned unavoidable beam movements. In order to minimize energy losses, one can consider the parameters for an all-fiber delivery system containing the cone on the exit and the energy homogenizer on the entrance. This system will allow for microsurgery in deeper lying tissues and internal organs, which is difficult or even impossible to accomplish with the articulated arm. We are able now to determine the parameters of such a fiber-based system and its limitations on the basis of the known properties of the fused silica fibers.

It is well known that color center formation occurs in fused silica fibers that have been subjected to repeated exposure of high power UV laser radiation. Color center formation results in a decrease of transmission with an increase of the number of laser pulses, and eventually transmission reaches some saturation level. This saturation effect is believed to be due to a finite number of defect sites which can result in color center formation. At an energy fluence 0.5 J/cm$^2$, fiber transmission decreased tenfold during the first 30 pulses up to a ≈0.1 cm$^{-1}$ and then the decrease became slower (R. K. Brimacombe, R. S. Tailor and K. ^E. Leopold J. Appl. Phys., 66, 4035(1989)).

It was found also that at 193 nm the fiber transmission begins to drop for single pulses with intensities as low as 1 MW/cm$^2$. The nonlinear absorption coefficient a was found to be approximately 2×10$^{-3}$ cm/MW (R. K. Brimacombe, R. S. Tailor and K. E. Leopold, J. Appl. Phys., 66, 4035 (1989)). This coefficient was independent within experimental error for different fiber types and thus, it was concluded that the coefficient is solely the property of the bulk material, which was fused silica. It is possible to evaluate the transmission of an ideal fiber when single photon absorption and color center formation are absent. In this case the change in fluence as a function of fiber length is given by (R. K. Brimacombe, R. S. Tailor and K. E. Leopold J., Appl. Phys., 66, 4035 (1989)):

$$-1/F x dF/dx = Fx a, \quad \text{(Eq. 1)}$$

where F is an energy fluence, x is the length of a fiber, and a is a non-linear absorption coefficient.

Integration of this differential equation results in the following dependence of the exiting energy fluence F on the entering fluence $F_0$ and a fiber length L:

$$F = 1/\gamma a L + 1/F_0 \quad \text{(Eq. 2)}$$

Figure 5:
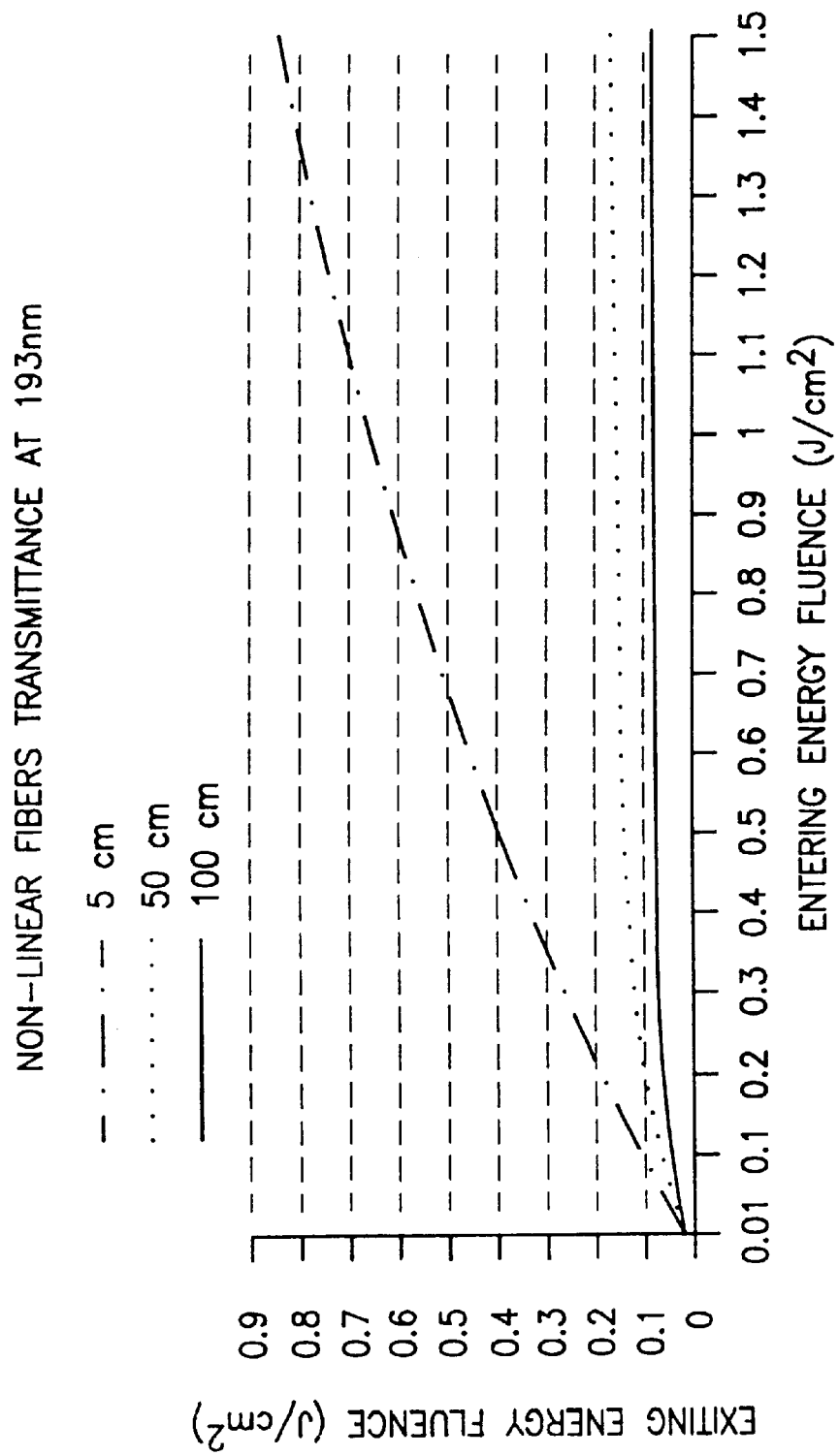
FIG. 5 is a graph illustrating the calculated dependence of an idealized quartz fiber transmission at 193 nm on the energy fluence for various fiber lengths.

This function is presented in FIG. 5 for three different lengths: 5, 50 and 100 cm. It is evident that the exiting energy fluence reaches some saturation level that depends on the fiber length. It is impossible, for example, to obtain more than 0.2 J/cm$^2$ at the exit of a 50 cm fiber. This observation shows that even through ideal quartz fiber it is impossible to obtain enough energy fluence for the ArF laser for microsurgical applications. One way to increase the efficiency of radiation delivery through such a fiber is to lower the energy fluence by increasing the core diameter.

For microsurgical applications however, only fibers that are not thicker than 1 mm can be used since thicker fibers are too rigid. At this diameter through an ideal fiber of 1 m in length and an entrance fluence of 0.4 J/cm$^2$/pulse it is possible to obtain an exit energy fluence of 80 mJ/cm$^2$/pulse. By tapering the end of the fiber as it is described in paragraph 6.1 it is possible to concentrate the energy. Thus, a tip with a 0.3 mm diameter exit and with a cone angle that does not exceed 0.2 the exiting radiation will be concentrated to 700 mJ/cm$^2$/pulse. This fluence is even higher than is required for effective cutting of soft tissues in a liquid environment. Thus, in spite of the strong multiphoton absorption of fused silica with nanosecond 193 nm excimer laser pulses, it is possible to use such fibers as a flexible delivery system if the amount of defect sites that result in color center formation are sufficiently decreased. The proper choice of parameters (such as entering energy fluence, fiber diameter and tip diameter) makes a fiber-based delivery system more convenient and effective for microsurgical applications of this laser than an articulated arm.

6.4 Applications of the Device.

Numerous applications of the present device are possible in the field of soft tissue microsurgery. One of the most promising of them is vitreoretinal membrane removal, because the accepted mechanical peeling and cutting of such membranes is often associated with retinal damage. Furthermore the present device can be used in all microsurgical procedures, including microsurgery of the internal organs. In addition, the technique can be used in cell microsurgery, such as drilling of the zona pellucida of oocytes for in vitro fertilization.

7. Experiments.

Several experiments were completed in order to demonstrate the efficiency of the device in vitreoretinal surgery in vivo and in vitro. We used 4.5 cm long pieces of Fiberguide G fibers with a core diameter of 0.8 mm coupled to the articulated arm. They each had a 2 mm tapered tip at the end with a 0.2 to 0.3 mm aperture. The entrance plane of these fibers tips was ground with grinding paper (particle size less than 20 micron). The energy fluence output from the tip was in the range 150 to 500 $mJ/cm^2/pulse$. It was shown that it is possible to cut retinal tissue and vitreoretinal membranes at a rate of 1 to 2 mm/s with a pulse repetition rate of 20 Hz. Characteristic width of these cuts was 100 to 200 microns. The cut depth was shown to be controlled by the energy fluence and by the number of pulses. It was also found that the cutting occurred only when the tip was in contact with the tissue. The absence of observable damage when the retina was irradiated without contact demonstrates that vitreal membranes can be safely removed from the retina when they are separated by even a thin layer of liquid. These experiments are the first step in demonstrating a variety of delicate surgical procedures that will evolve as a result of the application of this new device and method.

We claim:

1. A device for delivery of an ArF excimer laser beam for microsurgery, comprising:
   an elongated, fused silica optical fiber having a conical end portion having an inlet end with a first diameter and an outlet end with a second diameter, said fiber having an energy fluence threshold at which laser light from an excimer laser tends to damage the fiber;
   an exit aperture at said outlet end, said exit aperture having a diameter which is smaller than the diameter of said inlet end, said conical portion of said fiber serving as an energy fluence concentrator for an excimer laser beam supplied to said inlet end;
   a scattering surface in said fiber prior to said inlet end of said conical portion for scattering the laser beam supplied to the inlet end to increase the divergence of, and to produce peak energy broadening in, the laser beam supplied to said concentrator, the scattering surface being selected to maximize the energy fluence of the exit beam while maintaining an energy fluence level within the tapered portion which is below said threshold; and
   said conical portion being tapered inwardly from its inlet end to its outlet end to concentrate the laser beam to permit an increase in energy fluence at the exit aperture which is sufficient to permit ablation of materials in soft tissue microsurgery by the exit beam.

2. A device as recited in claim 1, further including a concentric tube around said tapered portion of said fiber to provide mechanical protection of the tapered portion and to permit lifting irradiated tissue and evacuation of gas bubbles and tissue debris that result from laser/tissue interactions.

3. A device as recited in claim 1, wherein said fiber is a UV grade fused silica having a very high nonlinear absorption coefficient at a wavelength of 193 nm and wherein said concentrator and said scattering surface cooperate to increase the intensity of said exit beam for an excimer laser beam at 193 nm.

4. A device as recited in claim 1, wherein said conical end portion inlet end has a first diameter of less than about 1 mm, and wherein said end portion tapers continuously inwardly to a second diameter of about 0.3 times said first diameter, and wherein said exit aperture has a diameter of about 0.3 mm.

5. A device as recited in claim 1, wherein said fused silica fiber has an absorption coefficient which limits light transmission through the fiber.

6. A device as recited in claim 5, wherein said exit aperture has a diameter of 0.3 mm.

7. A device as recited in claim 1, wherein said scattering surface has an optical roughness selected to maximize the energy fluence at the exit aperture while maintaining an energy fluence level in said tapered portion of said fiber below said threshold of damage.

8. A device as recited in claim 7, wherein said fiber has a thickness of less than about 1 mm, said exit aperture has a diameter of about 0.3 mm, and said tapered end portion has a length of about 2 mm.

9. A method for delivering a high flux of excimer laser light at a wavelength of 193 nm through an elongated UV grade fused silica fiber having a very high nonlinear absorption coefficient at 193 nm to a microsurgical target for ablation of materials in highly absorbing liquid and gaseous environments while preventing damage to the fiber, comprising:
   delivering to said fused silica fiber a beam of high flux ArF excimer laser light at a wavelength of 193 nm and at an intensity that would normally produce energy peaks above a threshold of damage in the flux;
   concentrating the laser light within a tapered portion of the fiber as the light propagates from an inlet end to an exit end of the tapered portion;
   producing an exit beam at an aperture at the exit end of the tapered portion; and
   scattering the exicimer laser light delivered to the inlet end of the tapered portion to increase entering beam divergence at said tapered portion to provide an angle of distribution which lowers the intensity and broadens the peaks of energy distribution of the beam entering the tapered portion by an amount determined by the damage threshold of the fiber, the angle of taper, and the relative diameters of inlet and outlet ends of the tapered portion of the fiber, thereby permitting the total energy transmitted through the tapered portion to be increased without exceeding the damage threshold of the fiber.

10. A method as recited in claim 9, further including:
    surrounding the exit aperture of the tapered fiber by a concentric tube around a tapered fiber tip incorporating the exit aperture to provide mechanical protection of the tapered fiber tip for lifting irradiated tissue and evacuating gas bubbles and tissue debris that result from laser/tissue interactions.

11. The method of claim 9, wherein scattering said beam includes grinding an entrance surface of said inlet of said tapered portion to produce a scattering surface so that high energy fluences can be introduced into the fiber without damaging the fiber by hot spots of energy inside the fiber as a result of either non-ideal fiber orientation or as a result of inhomogeneity of the laser beam, or as a result of beam interference inside the fiber.

* * * * *